(12) United States Patent
Shirvan et al.

(10) Patent No.: US 7,605,182 B2
(45) Date of Patent: Oct. 20, 2009

(54) COMPOUNDS THAT SELECTIVELY BIND TO MEMBRANES OF APOPTOTIC CELLS

(75) Inventors: Anat Shirvan, Herzliya (IL); Ilan Ziv, Kfar Saba (IL)

(73) Assignee: Aposense Ltd., Petach-Tikva (IL)

( * ) Notice: Subject to any disclaimer, the term of this patent is extended or adjusted under 35 U.S.C. 154(b) by 368 days.

(21) Appl. No.: 10/554,926

(22) PCT Filed: May 2, 2004

(86) PCT No.: PCT/IL2004/000366

§ 371 (c)(1),
(2), (4) Date: Oct. 31, 2005

(87) PCT Pub. No.: WO2004/096120

PCT Pub. Date: Nov. 11, 2004

(65) Prior Publication Data

US 2007/0031326 A1 Feb. 8, 2007

Related U.S. Application Data

(60) Provisional application No. 60/524,082, filed on Nov. 24, 2003.

(30) Foreign Application Priority Data

May 1, 2003 (IL) ..................................... 155723

(51) Int. Cl.
*A61K 31/194* (2006.01)
*C07C 55/02* (2006.01)

(52) U.S. Cl. ...................... 514/574; 562/489; 562/490; 424/1.37; 424/9.1; 514/557; 514/561

(58) Field of Classification Search ................ 514/557, 514/574; 562/490, 489, 488; 424/1.37, 9.1
See application file for complete search history.

(56) References Cited

FOREIGN PATENT DOCUMENTS

JP 42-17516 9/1967

OTHER PUBLICATIONS

International Search Report for Application No. PCT/IL2004/00366 mailed Jan. 31, 2005.
Paquette L.A. and Carmody M.J., "Thermal isomerization reactions of cis-9,10-dihydronaphthalene derivatives". Journal of the American Chemical Society, 1975, 97(20), 5841-5850.
Tan W.H. et al., "Molecular Recognition of Naphthalenedicarboxylic Acid Regioisomers by Cyclodextrins". Bulletin of the Chemical Society of Japan, 1998, 71 (6), 1285-1292.
Acton N. et al., "Preparation and oxidation of the bis(tetra-n-butylammonium) salt of 2,2'-(2,7-pyrenediyl)bis(propanedinitrile) dianion". The Journal of Organic Chemistry, 1982, 47 (6), 1011-1018.
Toshihiro K., Nobuhide W., "A New Synthesis of 1,4,5,8-Tetramethylnaphthalene". Synthesis, 1990, Issue 10, 967-968.
Ando T. and Nakagawa M., "Cyclic Acetylenes. X. A Transannular Hypochromism Observed in a Cyclic Diacetylene Containing a Naphthalene Nucleus". Bulletin of the Chemical Society of Japan, 1967, 40 (2), 363-370.
Peacock S.C. et. al., "Host-guest complexation. 13. High chiral recognition of amino esters by dilocular hosts containing extended steric barriers". Journal of the American Chemical Society, 1978, 100 (26), 8190-8202.
Grigg R. et. al., "X=Y-ZH systems as potential 1,3-dipoles. Part 1. Background and scope". J. Chem. Soc., Perkin Trans. 1, 1984, 41-46.
Andrés J.M. et. al., "Easy preparation of enantiopure $C_2$-symmetrical aminoalcohols derived from m-xylylene diamine". Tetrahedron: Asymmetry. 1994, 5 (1), 57-66.
van der Sluis M. et. al., "Diastereoselective Addition of Allylzinc Bromide to Imines Derived from (R)-Phenylglycine Amide". Organic Letters, 2001, 3 (24), 3943-3946.
Boesten W.H.J. et. al., "Asymmetric Strecker Synthesis of α-Amino Acids via a Crystallization-Induced Asymmetric Transformation Using (R)-Phenylglycine Amide as Chiral Auxiliary". Organic Letters, 2001, 3 (8), 1121-1124.

*Primary Examiner*—Charanjit S Aulakh
(74) *Attorney, Agent, or Firm*—Pearl Cohen Zedek Latzer, LLP (57) ABSTRACT

The invention relates to compounds that selectively bind to phospholipid membranes having the features of membranes of apoptotic cells, pharmaceutical compositions comprising the same and therapeutic and diagnostic methods using thereof.

15 Claims, 2 Drawing Sheets

COMPOUNDS THAT SELECTIVELY BIND TO MEMBRANES OF APOPTOTIC CELLS

PRIOR APPLICATION DATA

This application is a National Phase application of PCT International Application No. PCT/IL2004/000366, International Filing Date: May 2, 2004, claiming priority from Israel Patent Application Serial Number 155723, entitled "NOVEL COMPOUNDS THAT SELECTIVELY BIND TO MEMBRANES COMPRISING PHOSHPATIDYLSERINE" filed May 1, 2003 and U.S. Provisional Patent Application Ser. No. 60/524,082, entitled "NOVEL COMPOUNDS THAT SELECTIVELY BIND TO MEMBRANES COMPRISING PHOSHPATIDYLSERINE" filed Nov. 24, 2003, all of which are incorporated by reference in their entirety.

FIELD OF THE INVENTION

The invention relates to compounds that selectively bind to phospholipid membranes having the features of membranes of apoptotic cells, pharmaceutical compositions comprising the same, and therapeutic and diagnostic methods using thereof.

BACKGROUND OF THE INVENTION

Plasma membrane (the outer membrane) of intact eukaryotic cells is a phospholipid bilayer, characterized by an asymmetrical distribution of its phospholipid constituents between the inner and outer membrane leaflets. Thus, the aminophospholipids phosphatidylserine (PS) and phosphatidylethanolamine (PE), (particularly PS) reside almost entirely in the inner leaflet of the plasma membrane. This asymmetry of phospholipid distribution is important for various cellular functions, including normal cell interaction with its environment. This phospholipid asymmetry of plasma membrane is normally maintained, in an energy-dependent manner, by at least two systems comprising (1) an inward-directed pump, called the aminophospholipid translocase, which specifically and continuously moves PS and PE from the outer to the inner membrane leaflet in an ATP-dependent manner, while being inhibited by $Ca^{2+}$, and (2) an outward directed floppase, that moves mainly PS from the inner to the outer membrane leaflet.

While maintenance of this membrane organization is fundamental to normal cell physiology, cells undergoing apoptosis or other modes of cell death, and cells undergoing activation (e.g., platelets during the process of blood clotting) manifest a dramatic process of "scrambling" of membrane phospholipids, with loss of their asymmetrical distribution and exposure of PS on the cell surface. The major factors responsible for this phenomenon comprise inhibition of the aminophospholipid translocase, and activation of phospholipid scramblase, a powerful, $Ca^{2+}$ dependent protein system facilitating rapid bi-directional movement of phospholipids between the membrane leaflets.

Scrambling of membrane phospholipids and exposure of PS on the cell surface plays an important role in recruitment of macrophages for engulfment and removal of the apoptotic cells. In addition, phospholipid scrambling occurring in platelets plays an important role in rendering their surface a powerful catalytic platform for the assembly of several clotting factor complexes, such as the tenase and prothrombinase complexes. Accordingly, a strong correlation has been recently drawn between phospholipid scrambling and potent procoagulant effects exerted by apoptotic cells.

While these alterations have an important role in normal physiology, they may also be a factor in the pathogenesis of medical disorders associated with an abnormal, excessive blood clotting in numerous disorders such as arterial or venous thrombosis or thrombo-embolism (e.g., cerebral stroke, myocardial infarction, deep vein thrombosis, etc).

In addition to the plasma membrane of the cell, which manifests exposure of PS and an increased level of PE on the cell surface (i.e. on the outer leaflet of the plasma membrane) only upon phospholipid scrambling, many intracellular membranes (e.g., membranes of the endoplasmic reticulum) manifest such features on their surface as part of their normal structure. Cells wherein the plasma membrane is a PS-exposing membrane may be, for example, apoptotic cells or activated platelets. By contrast the plasma membrane of normal, healthy cells is not a PSE membrane, and thus these cells are not considered PSE cells.

It is desirable to have pharmaceutical agents, which have low molecular weight, and are capable of selective targeting, binding and potential accumulation within PSE cells.

BRIEF DESCRIPTION OF THE DRAWINGS

FIG. 1(A and B) demonstiates flow-cytometric analysis, showing selective binding of NST 892 to Jurkat cells undergoing apoptosis, induced by anti-Fas Ab;

FIG. 2(A and B) demonstrates selective binding of NST 892 in vivo to tumor cells undergoing cell death.

SUMMARY OF THE INVENTION

In order to address the above needs, the invention provides small-molecule agents, capable of selective binding to PSE membranes and PSE-cells. In another embodiment of the invention, there is provided a pharmaceutical composition comprising the agents, and diagnostic and therapeutic methods utilizing them.

The term "PS-exposing membrane" ("PSE-membrane") refers, in an embodiment of the invention to a phospholipid membrane comprising and exposing phosphatidylserine (PS) on its surface; and/or a phospholipid membrane which has increased amounts of PE in its outer leaflet, compared to the amount of PE in the outer leaflet of the plasma membrane of a healthy, normal cell. In an embodiment of the invention, the membrane is the plasma membrane of a cell, which undergoes phospholipid scrambling and loss of the normal asymmetry of phospholipid distribution. In addition, membranes of various intracellular organelles, such as the mitochondria or endoplasmic reticulum manifest exposure of PS and PE on their surface. Therefore, such membranes are also included within the scope of PSE-membranes.

The term "PSE-cell" refers to a cell, wherein the plasma membrane is a PSE-membrane. In an embodiment of the invention, the cells are selected from apoptotic cells, cells undergoing other types of cell death, and activated platelets.

The term "selective binding" refers in an embodiment of the invention to binding of the compound to PSE-cells, which is at least 30% higher than the binding of same compound to healthy, non-PSE cells.

The term "PSE-cells-binding compound" ("PSBC") refers to a compound that binds selectively to PSE-cells, i.e., manifests in an embodiment of the invention at least 30% higher binding to a PSE-cell, compared to its binding to normal cells.

The term "PSE-cells-binding conjugate" ("PSB-conjugate" or "Conjugate") refers in an embodiment of the invention, to a PSBC as defined above, linked to a medicinally-useful agent, which may be in one embodiment a marker for imaging, or in another embodiment, a drug. The PSB conjugate or the "conjugate" (as interchangeably used herein) targets the medicinally-useful agent selectively to the PSE cells, and thus enables the desired medical effect of either imaging or detection of PSE cells, or treating/ameliorating/preventing or reducing a disease process or a disorder associated with occurrence of PSE cells.

This invention provides, according to one of its aspects, compounds represented by the structure set forth in formula (I):

including pharmaceutically acceptable salts, solvates and hydrates of the structure of formula (I), wherein:

A is selected from:

(i) a moiety of the following represented by the structure set forth in formula II, wherein Z represents a ring system selected from aryl, heteroaryl, cycloalkyl, heterocyclyl, and combinations thereof, wherein the ring system consisting of 4, 5, 6, 7, 8, 9 or 10 atoms and X represents CR, $CH_2$, N, NH, O or S; and Y is selected among hydrogen, halogen and $-NO_2$; and (ii) a metal chelate comprising a metal and a metal chelator, wherein the metal is a radioisotope of a transition metal, or an oxo-derivative of such transition metal; and wherein the metal chelator is a moiety comprising metal coordinating atoms selected from N and S, connected one to another by linear or branched alkylene linkers of 2 or 3 carbon atoms each;

$L^1$ and $L^2$ are each independently selected from null and a $C_1$, $C_2$ or $C_3$, alkylene, where in case of a $C_3$ alkylene it may be a linear or branched alkylene;

$R^1$ and $R^2$ are each independently selected from a radical according to the structure set forth in formula (III):

wherein $R^3$, $R^4$ and $R^6$ are each independently selected from hydrogen, $C_1$, $C_2$, $C_3$, $C_4$, $C_5$ or $C_6$ alky, $C_1$, $C_2$, $C_3$, $C_4$, $C_5$ or $C_6$ hydroxyalkyl, $C_1$, $C_2$, $C_3$, $C_4$, $C_5$ or $C_6$ haloalkyl, 5 or 6 atom aromatic or heteroaromatic ring, amino-naphthalene-1-sulfonyl where the amino may be substituted by one or two alkyl groups, and combinations thereof, where the asterisk shows the bonding to $L^1$ or $L^2$.

In the above formula (I), in case that A is an aromatic ring system as showed in item (i) above, $L^1$ and $L^2$ ate each connected to A via substitution of any of the hydrogen atoms linked to the aromatic rings of A. In the case that A is a metal chelate as showed in item (ii) above, $L^1$ and $L^2$ are each connected to A via either the coordinating atoms or the alkylene linkers.

In an embodiment of the invention, the transition metal comprised in the chelate is selected from technetium, rhenium and the oxo-derivatives of these metals.

In an embodiment of the invention, the compounds of the invention have the following formula (IV):

including pharmaceutically acceptable salts, solvates, hydrates and optical isomers of the structure of formula (IV), wherein $R^3$, $R^4$, $R^6$, $L^1$ and $L^2$ are as described in formula I above.

In another embodiment, the compounds of the invention have the following formula (V):

including pharmaceutically acceptable salts, solvates, hydrates and optical isomers of the structure of formula (V), wherein $R^3$, $R^4$ and $R^6$ may be the same or different, and are each selected from hydrogen; $C_1$, $C_2$, $C_3$, $C_4$, $C_5$ or $C_6$ alkyl; $C_1$, $C_2$, $C_3$, $C_4$, $C_5$ or $C_6$ hydroxyalkyl; and $C_1$, $C_2$, $C_3$, $C_4$, $C_5$ or $C_6$ fluoroalkyl.

In the case that the compound has the structure of formula V, wherein $R^3$ and $R^4$ are each a hydrogen and $R^6$ are each a butyl, the compound is designated NST895.

In another, embodiment, the compound of the invention has the structure as set forth in formula (VI):

(VI)

including pharmaceutically acceptable salts, solvates, hydrates and optical isomers of the structure of formula (VI), wherein b stands for an integer of 2,3,4,5 or 6.

In another embodiment, the compound of the invention has the structure as set forth in formula (VII):

(VII)

including pharmaceutically acceptable salts, solvates, hydrates and optical isomers of the structure of formula (VII), wherein m and n each stands independently for an integer of 1, 2, 3 or 4, and k stands for an integer of 2, 3, 4 or 5.

In another embodiment, the compound of the invention has the structure set forth in formula VIII:

(VIII)

including pharmaceutically acceptable salts, solvates, hydrates and optical isomers of the structure of formula (VIII), wherein M is a metal atom selected from 99m-Technetium and Rhenium; $R^3$ and $R^4$ may each be the same or different and are selected from hydrogen and $C_1$, $C_2$, $C_3$, $C_4$, $C_5$ or $C_6$ alkyl.

In an embodiment of the invention, M is an atom of 99m-Tc, $R^4$ are each a butyl group, and $R^3$ are each a hydrogen.

In another embodiment, the compound of the invention has the structure set forth by formula IX:

(IX)

including pharmaceutically acceptable salts, solvates, hydrates and optical isomers of the structure of formula (IX). This compound is designated NST-892.

In another embodiment of the invention, there is provided a method of using the compounds of the invention, or conjugate thereof for detection of PSE cells, diagnosis of diseases associated with PSE cells in the body, or targeting of pharmaceutical agents to foci of disease in the body, for the treatment or prevention of disease, wherein the foci of disease comprise PSE cells.

DETAILED DESCRIPTION

This invention provides, according to one of its aspects, compounds represented by the structure set forth in formula (I):

$$R^1\text{-}L^1\text{-}A\text{-}L^2\text{-}R^2 \tag{I}$$

including pharmaceutically acceptable salts, solvates and hydrates of the structure of formula (I), wherein:

A is selected from:

(i) a moiety of the following represented by the structure set forth in formula II, (II)

wherein Z represents a ring system selected from aryl, heteroaryl, cycloalkyl, heterocyclyl, and combinations thereof, the ring system consisting of 4, 5, 6, 7, 8, 9 or 10 atoms and X represents CH, $CH_2$, N, NH, O or S; and Y is selected among hydrogen, halogen and —NO$_2$; and (ii) a metal chelate comprising a metal and a metal chelator, wherein the metal is a radioisotope of a transition metal, or an oxo-derivative of such transition metal; and wherein the metal chelator is a moiety comprising metal coordinating atoms selected from N and S, connected one to another by linear or branched alkylene linkers of 2 or 3 carbon atoms each;

$L^1$ and $L^2$ are each independently selected from null and a $C_1$, $C_2$ or $C_3$, alkylene, where in case of a $C_3$ alkylene it may be a linear or branched alkylene;

$R^1$ and $R^2$ are each independently selected from a radical according to the structure set forth in formula (III):

(III)

wherein $R^3$, $R^4$ and $R^6$ are each independently selected from hydrogen, $C_1$, $C_2$, $C_3$, $C_4$, $C_5$ or $C_6$ alkyl, $C_1$, $C_2$, $C_3$, $C_4$, $C_5$ or $C_6$ hydroxyalkyl, $C_1$, $C_2$, $C_3$, $C_4$, $C_5$ or $C_6$ haloalkyl, 5 or 6 atom aromatic or heteroaromatic ring, amino-naphthalene-1-sulfonyl where the amino may be substituted by one or two alkyl groups, and combinations thereof, where the asterisk shows the bonding to $L^1$ or $L^2$.

In the case that A is an aromatic ring system, as defined in item (i) above, $L^1$ and $L^2$ are each connected to A via substitution of any of the hydrogen atoms linked to the aromatic rings. In the case that A is a metal chelate as defined in item (ii) above, $L^1$ and $L^2$ are each connected to A via either the coordinating atoms or the alkylene linkers.

In an embodiment of the invention, the transition metal comprised in the chelate is selected from technetium, rhenium and the oxo-derivatives of these metals.

In an embodiment of the invention, the compounds of the invention have the following formula (IV):

(IV)

including pharmaceutically acceptable salts, solvates, hydrates and optical isomers of the structure of formula (IV), wherein $R^3$, $R^4$, $R^6$, $L^1$ and $L^2$ are as described in formula I above.

In another, embodiment, the compounds of the invention have the following formula (V):

(V)

including pharmaceutically acceptable salts, solvates, hydrates and optical isomers of the structure of formula (V), wherein $R^3$, $R^4$ and $R^6$ may be the same or different, and are each selected from hydrogen; $C_1$, $C_2$, $C_3$, $C_4$, $C_5$ or $C_6$ alky; $C_1$, $C_2$, $C_3$, $C_4$, $C_5$ or $C_6$ hydroxyalkyl; and $C_1$, $C_2$, $C_3$, $C_4$, $C_5$ or $C_6$ fluoroalkyl.

In the case that the compound has the structure of formula V, wherein $R^3$ and $R^4$ are each a hydrogen and $R^6$ are each a butyl, the compound is designated NST895.

In another embodiment, the compound of the invention has the structure as set forth in formula (VI):

(VI)

including pharmaceutically acceptable salts, solvates, hydrates and optical isomers of the structure of formula (VI), wherein b stands for an integer of 2,3,4,5 or 6.

In another embodiment, the compound of the invention has the structure as set forth in formula (VII):

including pharmaceutically acceptable salts, solvates, hydrates and optical isomers of the structure of formula (VII), wherein m and n each stands independently for an integer of 1, 2, 3 or 4, and k stands for an integer of 2, 3, 4 or 5.

In another embodiment, the compound of the invention has the structure set forth in formula VIII:

(VIII)

including pharmaceutically acceptable salts, solvates, hydrates and optical isomers of the structure of formula (VIII), wherein M is a metal atom selected from 99m-Technetium and Rhenium; $R^3$ and $R^4$ may each be the same or different and are selected from hydrogen and $C_1$, $C_2$, $C_3$, $C_4$, $C_5$ or $C_6$ alkyl.

In an embodiment of the invention, M is an atom of 99 m-Tc, $R^4$ are each a butyl group, and $R^3$ are each a hydrogen.

In another embodiment, the compound of the invention has the structure set forth by formula IX:

(IX)

including pharmaceutically acceptable salts, solvates, hydrates and optical isomers of the structure of formula (IX). This compound is designated NST-892.

The compounds of the invention may be linked, in an embodiment of the invention, either directly, or via a linker, wherein the linker is selected from a $C_1$, $C_2$, $C_3$, $C_4$, $C_5$ or $C_6$ alkylene, 5 or 6 atom aromatic or heteroaromatic ring, a metal chelator and combinations thereof, to any one of the following agents or to combination thereof, thus creating a "PSE-cells-binding conjugate" ("PSB-conjugate" or "Conjugate"), wherein the agents may be as follows:

1 Marker for imaging, selected from a detector of color, fluorescence, x-ray, CT scan, magnetic resonance imaging (MRI) and radio-isotope scan such as single photon emission tomography (SPECT) or positron emission tomography (PET);

2 A drug, for the prevention, amelioration or treatment of a specific disease which manifests PSE cells. The drug may be selected, without being limited from the following group: (i) An inhibitor of apoptosis, (e.g., caspase inhibitor; antioxidant, modulator of the Bcl-2 system); (ii) An activator of cell death, an inducer of apoptosis (e.g., an anticancer drug); (iii) A modulator of blood coagulation, selected from an anticoagulant, an antithrombotic, or a thrombolytic agent. In such a case, the drug may be selected from an antiplatelet agent, heparin, low molecular weight heparin, antagonists of glycoprotein IIb/IIIa, tissue plasminogen activator (tPA), or an inhibitor of a clotting factor, such as an inhibitor of thrombin or an inhibitor of factor Xa; (iv) An anti-inflammatory drug or an immuno-modulator drug; or (v) may comprise or may be linked to a radioisotope which has therapeutic effects. Examples for such isotopes, without limitation, are Yittrium 90, Iodine 131, Rhenium 188, Holmium 166, Indium 111, Leutitium 177, or any other radioisotopes emitting radiation useful for therapeutic purposes. The conjugate enables the targeting of the drug to the PSE cells.

3. A Solid Support:

According to some embodiments of the invention, the compounds of the invention may be used for selective targeting of a compound to a PSE-cell in a cell population, comprising the step of: (i) contacting the cell population comprising the PSE-cell with a compound or a conjugate comprising the compound; thereby selectively targeting the compound or the conjugate comprising the compound to the PSE-cell within the cell population.

In accordance with some embodiments of the invention, the invention may be used for the detection of PSE-cells. According to this approach, there is provided a composition comprising as an effective ingredient a PSB-conjugate as defined above, comprising a marker for imaging, for the detection of PSE-cells in a sample, either in vitro, ex vivo or in vivo and a pharmaceutically acceptable carrier. Such a PSB-conjugate, which may be used for detection or imaging, is termed diagnostic PSBC.

The marker for imaging may be in an embodiment of the invention a chromophore, a fluorescence-emitting moiety, a radio-label, a label capable of undergoing an enzymatic reaction producing a detectable color, a marker for x-ray, a marker for MRI or a marker for radio-isotope imaging, such as single photon emission tomography (SPECT) or positron emission tomography (PET scan). The diagnostic PSBC of the invention enables the targeting of the marker, through the action of the PSBC, to PSE-cells in a selective manner. Then, the detectable label can be detected by any manner known in the art, and in accordance with the specific label used, for example, fluorescence, radioactive emission, or a color production, MRI, x-ray and the like. The term "bound" refers to covalent or non-covalent (e.g., electrostatic) binding, which connects the PSBC to the detectable label.

In an embodiment of the invention, the detectable label is selected among the metal isotopes Tc, In, Cu, Ga, Xe, Tl and Re and the covalently linked atoms: $^{123}$I and $^{131}$I for radio-isotope scan, Gd(III), Fe(III) or Mn(II) for MRI and $^{18}$F, $^{15}$O, $^{18}$O, $^{11}$C, $^{13}$C, $^{124}$I, $^{13}$N and $^{75}$Br for Positron Emission Tomography (PET) scan.

In an embodiment of the invention, the diagnostic PSBC is aimed at clinical imaging of apoptosis via PET scan. The diagnostic PSBC may comprise in an embodiment of the invention, $^{18}$F atom(s), being linked to the PSBC either directly or through a linker as defined above.

Since the attachment of $^{18}$F for the purposes of clinical imaging is often done as the last step of the synthesis, immediately before the administration of the diagnostic compound to the patient, it may be advisable to synthesize a PSBC-PET precursor, being a PSBC attached to a moiety to be substituted by $^{18}$F as a final step before imaging. In an embodiment of the invention, the moiety is a hydroxyl group, a nitro group, or a halogen atom such as bromine or chlorine. Such a PSBC-PET precursor is also included in the scope of the invention.

In an embodiment of the invention, wherein the market is a metal atom (e.g., Gd or $^{99m}$Tc), the PSB-conjugate comprises a metal chelator. In an embodiment of the invention, the metal coordinating atoms of the chelator are selected from nitrogen, sulfur and oxygen atoms. In another embodiment of the invention, the chelator, is selected from diaminedithiols, monoamine-monoamide-bisthiols (MAMA), triamide-monothiols, and monoamine-diamide-monothiols.

In such cases, both the PSBC-chelate precursor, being the PSBC attached to the chelator prior to complexation with the metal atom, and the complex comprising the metal atom are included in the scope of the invention.

In the case that the marker for imaging comprised within the diagnostic PSBC is a fluorescence-emitting moiety, the moiety may be a 5-(dimethylamino)naphthalene-1-sulfonylamide (dansyl-amide) group, linked to the PSBC either directly or via a linker as defined above.

The above adducts can be used for a detection and diagnosis of a wide variety of physiological conditions (including normal conditions), pathological conditions, diseases or disorders which are characterized by propagation of PSE cells.

Examples of diseases, disorders or physiological conditions characterized by PSE cells are as follows:

Diseases which are characterized by occurrence of excessive-apoptosis, such as degenerative disorders, neutodegenerative disorders (e.g., Parkinson's disease, Alzheimer's disease, Huntington chorea), AIDS, myelodysplastic syndromes, ischemic or toxic insults, graft cell loss during transplant rejection; tumors, and especially highly malignant/aggressive tumors, are also often characterized by enhanced apoptosis, in addition to the excessive tissue proliferation.

Diseases manifested by excessive blood clotting: these diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, auto-immune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Atherosclerotic plaques, and especially plaques that are unstable, vulnerable and prone to rupture, are also characterized by PSE cells, such as apoptotic macrophages, apoptotic smooth muscle cells, apoptotic endothelial cells, activated platelets and activated inflammatory cells.

The detection method may also be carried out to evaluate the severity of a related disease and in order to monitor response to a therapeutic agent. An example for such monitoring is evaluation of response to anticancer therapy. Since most anti-tumor treatments, chemotherapy or radiotherapy exert their effect by induction of apoptosis, detection by a diagnostic PSBC of therapy-induced apoptosis of tumor cells may teach on the extent of sensitivity of a tumor to the anti-tumor agent, thus substantially shortening the lag period between the time of administration of the anti-cancer-treatment and the time of proper assessment of its efficacy.

Moreover, the detection may be used also to monitor adverse effects of anti-cancer treatments. A large part of such adverse effects are due to untoward treatment-induced apoptosis of normal, yet sensitive cells, such as those of the gastrointestinal epithelium or the bone marrow hemnatopoietic system. Detection by the diagnostic PSBC of apoptosis in such tissues may allow early detection of this untoward tissue damage and better optimization of the treatment protocol.

In addition, the detection method may aim at characterization of the intrinsic apoptotic load within a tumor. The apoptotic load often correlates with the level of tumor aggressiveness. The detection method may also assist in the detection of metastases, via detection of apoptosis within the metastases.

Similarly, the diagnostic PSBC of the current invention may be useful in monitoring graft survival after organ transplantation, since apoptosis, potentially detectable by the diagnostic PSBC of the invention, plays a major role in cell loss during graft rejection.

In addition, the detection approach may be used for monitoring response to cyto-protective treatments, and accordingly may be used in screening and development of drugs which are capable of inhibiting cell loss in various diseases (for example those recited above) by enabling a measure of evaluation of cell death.

The detection may be also useful for the detection of atherosclerotic plaques, since destabilization of such plaques, rendering them vulnerable, prone to rupture, thrombosis and embolization, is characterized by participation of several types of PSE-cells, including apoptotic cells (apoptotic macrophages, smooth muscle cells and endothelial cells) and activated platelets.

The detection via the diagnostic PSBC of the invention may also take place for the purposes of basic research, in the study of apoptosis in tissue culture or in animal models.

In another embodiment, the present invention relates to a method for detecting PSE-cells in a patient or an animal in vivo, the method comprising:
  (i) administering a diagnostic PSBC, namely any compound of the invention which is linked to or comprises a marker for imaging or detection, to the examined patient or animal; the administration being performed by any means known in the art, such as parenteral (e.g., intravenous) or oral administration;
  (ii) imaging the examined patient or animal, by any imaging method known in of the art (e.g., PET scan, SPECT, MRI), to detect and determine the amount of diagnostic PSBC bound to cells, wherein a significant amount of compound bound a cell indicates its being a PSE cell.

In another embodiment of the invention, the present invention is related to a method for the detection of PSE-cells in a tissue or cell culture sample in vitro or ex-vivo, the method comprising:
(i) contacting the sample with a diagnostic PSBC under conditions enabling binding of the diagnostic PSBC to biological membranes of PSE-cells;
(ii) detecting the amount of bound PSBC to the cells; the presence of a significant amount of bound compound indicating the presence of PSE-cells in the sample.

The step of detection in the in vitro or ex-vivo studies may be for example, without limitation, by using flow cytometric analysis, which permits cell visualization on equipment that is widely commercially available.

The invention further provides a method of detecting cell death within a tumor in a suspected body area of an examined subject, the method comprising: (i) administering to the examined subject a compound according to the invention or a Conjugate thereof, wherein the compound or the Conjugate is being linked or comprises a detectable marker for imaging; and (ii) determining the amount of the compound bound to cells in the tumor or in the organ comprising the tumor, wherein a significant amount of the compound bound to cells in a suspected area indicates that these tumor cells are undergoing apoptosis.

The term "significant amount" according to the invention means that the amount of PSBC bound to a PSE-cell is at least 30% higher than the amount bound to a non-PSE-cell. In another embodiment of the invention, the amount may be at least 50%. In another embodiment, the amount may be at least 60%. In another embodiment, the amount may be at least 70%. In another embodiment, the amount may be at least 80%. In another embodiment, the amount may be at least 90%. In another embodiment, the amount may be at least 95%. In another embodiment, the amount may be at least 150%. In another embodiment, the amount may be at least 200%. In another embodiment, the may be more than 5 times than the binding to a non PSE-cell. The method for determining the actual amount may vary according to the imaging method and equipment utilized, and according to the organs or tissues examined.

The method of the present invention may be used for the diagnosis of a disease characterized by the occurrence of PSE-cells, for example, any one of the diseases indicated above. The method for detecting of PSE-cells in a patient or in an animal comprising the steps of: (i) administering to the patient or animal a compound according to the invention or a Conjugate of the compound linked to a marker for imaging; and (ii) imaging the patient or animal, so as to determine the amount of the compound or the Conjugate comprising the compound bound to the cells of the imaged organ, wherein a significant amount of diagnostic PSBC bound to a cell indicates its being a PSE-cell.

The method of the present invention may also be used for monitoring the effects of various therapeutic modalities used for treatment of the diseases or medical conditions, or alternatively for basic science research purposes as explained above.

In accordance with a another approach of the invention, the present invention concerns a pharmaceutical composition comprising a PSB-conjugate as an active ingredient, optionally with a pharmaceutically acceptable carrier; the PSB-conjugate being formed of (i) a medicinally-useful, pharmaceutically-active drug; and (ii) a PSBC. The PSB-conjugate may act to target the drug to PSE-cells, and can therefore be useful for the treatment of a disease characterized by the presence of PSE-cells as defined above. The PSB-conjugate is designated "therapeutic PSBC".

The association between the medicinally-useful drug and the PSBC comprising the therapeutic PSBC of the invention may be either by covalent binding, by non-covalent binding (e.g., electrostatic forces) or by formation of carrier particles (such as liposomes) comprising the drug and having on their surface a PSBC, which targets the complex to the PSE cells.

The purpose of a therapeutic PSBC is to direct the drug comprised within, selectively, only to PSE-cells and to tissues and organs comprising the cells. Once the drug reaches the target it should be able to exert its physiological activity, either when still being in the complex as part of the PSB-conjugate, after disconnecting from the PSBC unit (for example by cleavage, destruction, activity of natural enzymes, etc), by phagocytosis of a drug-containing liposome having PSBC on its membrane, or by any other known mechanism.

The drug should be chosen in accordance with the specific disease for which the composition is intended.

In another embodiment of the invention, there is provided a method of targeting an anticoagulant or a fibrinolytic agent to a blood clot, comprising the step of administering a compound according to the invention, being linked to an anticoagulant or a fibrinolytic agent, thereby achieving targeting of the drug to the blood clot.

For treatment or prevention of diseases which are manifested by initiation or propagation of abnormal and excessive blood clotting [e.g., arterial or venous thrombosis, thromboembolism, sickle cell diseases, beta-thalassemia, antiphospholipid antibody syndrome, disseminated intravascular coagulation (DIC), thrombotic thrombocytopenic purpura (TTP), systemic lupus erythematosus], the drug should be a compound which is known to inhibit formation of blood clots, or to dissolve blood clots after they have been formed, such as an antiplatelet agent, heparin, low molecular weight heparin, antagonists of glycoprotein IIB/IIIA, tissue plasminogen activator (tPA), or an inhibitor of a clotting factor, such as an inhibitor of thrombin, or an inhibitor of factor Xa.

Where the disease is manifested by inappropriate and excessive apoptosis such as degenerative disorders, neurodegenerative disorders (e.g., Parkinson's disease, Alzheimer's disease, Huntington chorea), AIDS, myelodysplastic syndromes, ischemic or toxic insults, graft cell loss during transplant rejection), the drug should be capable of inhibiting apoptosis. Such a drug may be, among others, a caspase inhibitor, a modulator of the Bcl-2 system or an anti-oxidant.

Where the disease is an inflammatory disorder, and/or disease associated with immune-mediated etiology or pathogenesis, such as auto-immune disorders for example antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis, the drug should be an anti-inflammatory drug, or an immuno-modulator drug.

For the treatment or prevention of unstable atherosclerotic plaque, characterized by thrombosis or apoptosis, the drug can be chosen from the above groups of drugs.

In another embodiment of the invention, there is provided a method of targeting anticancer drugs to a tumor which has foci of apoptotic cells, the method comprising the step of administering a compound according to the invention, being linked to a cytotoxic drug, thereby achieving targeting of the drugs to the foci of cell death within the tumor.

The PSB-conjugate of the invention, comprising an anticancer drug may be used to enhance the efficacy of anticancer protocols. The enhancement of an anti-cancer protocol is achieved by either:

(1) Targeting of the conjugate to a tumor tissue; such tissue is often characterized by an abnormally excessive apoptotic load (the latter often being correlated to the level of tumor aggressiveness);

(2) Use of two waves of apoptosis: the first wave being achieved by using a standard chemotherapeutic or radiotherapeutic agent, aimed at initiating an apoptotic process within the tumor; followed by a second wave of apoptosis, in which the anticancer drug is administered as part of a PSB-drug conjugate, being targeted to the apoptotic cells produced by the first wave. Thus, augmentation of the local concentrations of the anticancer drug within the tumor mass is achieved, with consequent enhancement of the local tumor-killing process, while maintaining relatively lower levels of the drug in non-tumor tissues.

The pharmaceutical composition of the invention may be administered by any of the known routes, inter alia, oral, intravenous, intraperitoneal, intramuscular, subcutaneous, sublingual, intraocular, intranasal or topical administration. The carrier should be selected in accordance with the desired mode of administration, and include any known components, e.g. solvents; emulgators, excipients, talc; flavors; colors, etc. The pharmaceutical composition may comprise, if desired, also other pharmaceutically-active compounds which are used to treat the disease, eliminate side effects or augment the activity of the active component.

The present invention in accordance with this aspect, still further concerns a method for improvement of treatment of a disease manifested by PSE-cells, comprising administering to an individual in need of such treatment, an effective amount of a PSB-conjugate. The conjugate allows for selective targeting of the drug to the tissues comprising PSE-cells, thus augmenting its local concentration, and potentially enhancing its therapeutic effect at the target site.

The term "effective amount" refers to an amount capable of decreasing, to a measurable effect, at least one adverse manifestation of the disease and should be chosen in accordance with the drug used, the mode of administration, the age and weight of the patient, the severity of the disease, etc.

By another approach of the invention the properties of the PSBCs to bind specifically to PSE-cells are utilized to clear body fluid of the cells. Preferably, the body fluid is blood or a blood product.

According to this embodiment, the invention provides a PSBC immobilized on a solid support. The immobilization may be by direct attachment, either by covalent or non-covalent binding, or by attachment through a spacer. The immobilized PSBC is intended to clear a body fluid from PSE-cells.

The term "solid support" refers in the contents of the present invention to a solid matrix, an insoluble matrix, and an insoluble support. The solid support in accordance with the present invention may be formed in a variety of structures such as a stack of micro-particulates, micro-filters, or micro-capillara, and may be composed of various materials such as alumina, diatomaceous earth, celite, calcium carbonate, calcium sulfate, ion-exchange resin, silica gel, charcoal, amberlite, dowex, Eupergit and ethylsofoxycellulose.

The compounds immobilized on a solid support form part of a filter device. Thus in accordance with the clearance approach, the present invention further concerns a filter device comprising a housing containing the PSBC immobilized on the solid support, and a fluid inlet and fluid outlet. Body fluids such as blood or blood products enter the housing through the inlet, come into contact and adhere to the immobilized PSBC contained in the housing. Thus, the body fluid is cleared of circulating cells having perturbed membranes, such as damaged or dying cells, or cleared of larger structures such as emboli having PSE-membranes. Consequently, fluid exiting from the outlet has a reduced content of the PSE-cells or is essentially devoid of the same.

EXAMPLES

Example 1

Synthetic Scheme that Shows a Route for the Preparation of the Compounds of the Invention

REFERENCES

JACS, 1975, 97, 5841 (Step 1)

Bull Chem. Soc. Jpn. 1998, 1285-1292 (Step 1)

JOC. 1982, 1011-1018.; Synth, 1990, 967-968; Bull Chem Soc Jpn. 1967, 363-370 (Step 2)

JACS. 1978, 8190-8202; J. Chem. Soc Perkin Trans 1984, 41-46; Tetrahedron:Asymmetry, 1994, 57 (Step 4).

Org Lett 2001, 3, 3943-3946; Org. Lett. 2001, 3, 1121-1124. (Step 5a)

Example 2

Synthesis of Mono Dansyl Naphthalene Diglycine (NST-892)

Example 3

Synthesis of NST895

Compound 5 (15 g) was treated with n-hexyllithium and (Boc)₂O in THF for 2 h and 23 g (>99%) of tetra-Boc compound 6 was obtained after work-up. Previously prepared compound 6 (11.72 g, 1.0 eq) was treated with in-situ generated potassium diisopropylamine (KDA, 2.5 eq) and lithium tert-butoxide (LiOtBu, 2.5 eq) under −78° C. for 2 h 11 g of crude product was obtained after work-up and $^1$H NMR indicated that it composed of 1:1 ratio of starting material and desired product. The crude product was purified by precipitating out the starting material, using a mixed solvent of EtOAc/Heptane (50 mL/100 mL). This way, 5.74 g (40%) of product 7 was obtained in a purity of 80%. This product was then subjected to the deprotection conditions by treating with TFA (100 mL) at room temperature for 2 h. 6.7 g of crude product 8 was obtained after TFA was evaporated. This crude product was directly used in the next step.

Solution of 8 in methanol (25 mL) was added to a cooled mixture of methanol (50 mL) and thionyl chloride (40 mL, 50 eq). After overnight at room temperature, $^1$H NMR analysis of the reaction mixture showed only 25% of conversion. The reaction was then heated to 50° C. for 15 h. The reaction was concentrated to dryness and the residue was taken up in 150 mL of saturated NaHCO₃, extracted with DCM (3×100 mL). 2.1 g of crude product (HPLC purity 62.6%) was obtained after the organic extract was evaporated to dryness. The crude product was purified by column chromatography and 1.15 g (100% HPLC AUC, 49% for 2 steps) of bis-methyl ester 9 was isolated as a tan film. The methyl ester 9 was stable on silica gel column.

Reductive amination was then performed Compound 9 (130 mg, 1.0 eq) and butyraldehyde (2 eq) were mixed in 1,2-dichloroethane (2 mL), and then treated with Na(QAc)₃BH (2 6 eq). The mixture was stirred at rt under N₂ for 1.5 h before quenched with saturated NaHCO₃ aq. After work-up, 200 mg of crude product was obtained. $^1$H NMR, HPLC and MS analysis indicated a 5:1 ratio of desired product 10a and monoalkylated product (70% AUC vs. 14% AUC). This crude product was purified by column chromatography and 130 mg (72%) of compound 10a was isolated as a brownish film. This product was then treated with LiOH (8 eq) in a mixture of THF/H$_2$O. MS and HPLC analysis of the reaction mixture showed a complete and clean hydrolysis after 3 h at room temperature. A semi-prep HPLC method was used to purify the product NST895. 60 mg (50%) of pure compound NST895 was obtained as a white solid HPLC analysis showed the desired compound (combined AUC >99%) and $^1$H NMR matched the desired structure.

Example 4

Selective Binding of NST-892 to Apoptotic Jurkat Cells; Flow-cytometric (FACS) Analysis Experimental Procedures Cultured Jurkat cells (human adult T cell leukemia cells) were grown in suspension in RPMI medium (Beit-Haemek, Israel), supplemented with 10% of fetal calf serum (FCS), 4 mM of L-glutamine, 1 mM of sodium pyruvate, 1 mM CaCl$_2$ and antibiotics (100 units/ml penicilin; 100 μg/ml streptomycin and 12.5 units/ml of nystatin) Prior to induction of apoptosis, medium was replaced with HBS buffer (10 mM HEPES; 140 mM NaCl, 1 mM CaCl). Apoptosis was then triggered by treatment with anti-Fas Ab (0.1 μg/ml; 2.5 hrs). Both control cells and apoptotic cells were then incubated for 20 minutes with 500 μM of NST-892 dissolved in 0.1 m NaPpi pH=7.4. Subsequently, cells were co-stained with propidium iodide (PI), a marker of membrane disintegration during late phases of cell death, and the selective binding of the NST-892 compounds to control and apoptotic cells was determined by flow cytometric (FACS) analysis using Becton-Dickinson cell sorter and CellQuest software (excitation was at 356 nm and emission was measured at 530 nm).

Experimental Results

The analysis shown in FIG. 1 describes the uptake of the NST-892 compound into the population of apoptotic cells in control and anti-fas treated cultures.

Figure 1A:
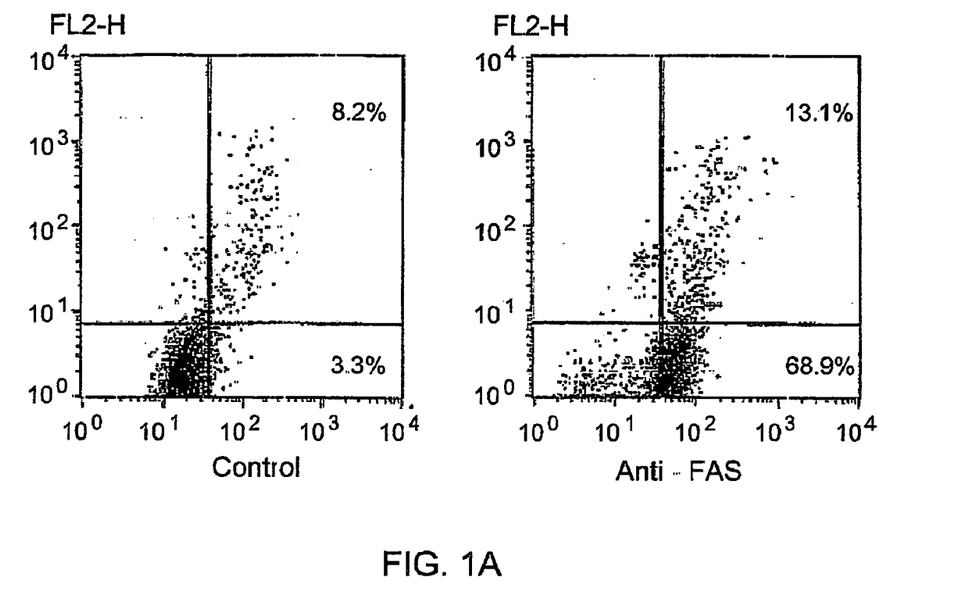

In the dot plot shown in FIG. 1A, the left lower quadrant represents the healthy, non-stained fraction of cells. The right lower quadrant represents the newly formed population of cells in the early stages of apoptosis. These cells still maintain membrane integrity and thus exclude PI. Cells binding both NST-892 and PI, i e., cells in the late stages of apoptosis are represented in the right upper quadrant.

Figure 1B:
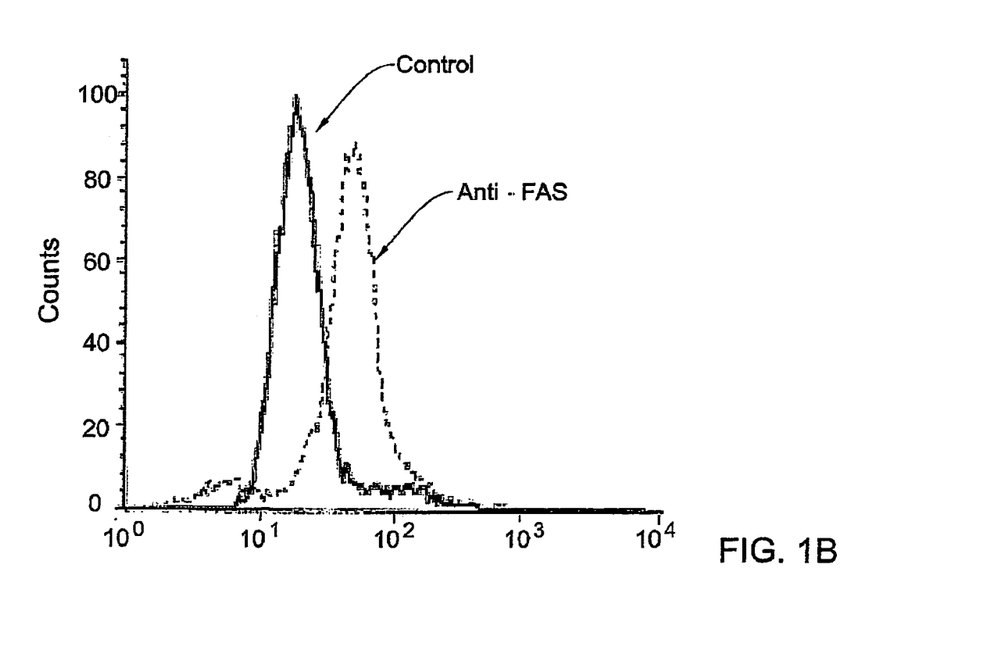

The induction of apoptosis was associated with the emergence of a marked, distinct population of cells in the early stages of the apoptotic process, selectively binding NST-892 and occupying the right lower quadrant of the plot. The percent of identified early apoptotic events within the population is 68.9% in the apoptotic cells as compared with 3.3% of the non-treated control cells. FIG. 1B is a histogram analysis of the data presented in FIG. 1A. The emergence of a new and distinct peak of highly fluorescent cells in the early phase of the apoptotic process is clearly associated with anti-Fas treatment.

Example 5

Targeting of NST 892 In-Vivo to Chemotherapy-induced Apoptotic Cells of Murine Melanoma Tumors in Mice Experimental Procedures Mice (c57/black; 8 weeks old male mice) were injected subcutaneously bilaterally, in the flank, with murine melanoma-derived B16-F10 cells (ATCC CRL-6475; $10^5$ cells/mice in a volume of 100 μl). Prior to injection, the cell line was maintained in culture in Dulbecco's modified Eagle's medium (DMEM), supplemented with 4 mM of L-glutamine; 100 units/ml of penicillin; 100 μg/ml of streptomycin; 12.5 units/ml of nystatin and 10% of fetal calf serum (FCS). After 10 days, when tumor diameter reached the size of 5-7 mm, mice were subjected to chemotherapy treatment (Taxol 20 mg/Kg together with Cyclophosphomid, 300 mg/Kg, in a volume of 200 μl intra-peritoneal injection). Twenty-four hours later, NST-892 was injected systemically at a dose of 2.8 mg/mouse in 10% chromophore in tris buffer. Two hours later, mice were sacrificed and tumors were frozen in liquid nitrogen as well as other organs were taken, and immediately frozen in liquid nitrogen. Uptake of NST-892 by the tumors or other organs was assessed by fluorescent microscopy analysis of frozen sections from each tissue.

Experimental Results

Figure 2A:
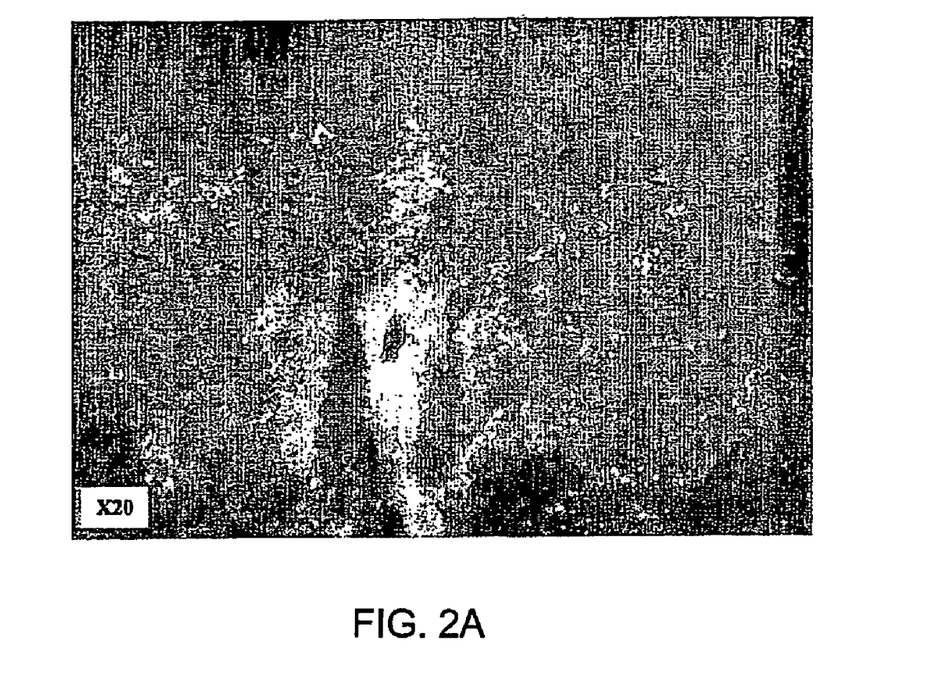

FIG. 2A. shows fluorescent microscopy of the tumor. Extensive binding of NST-892 to numerous tumor cells undergoing apoptosis can be observed. Demonstrated are also the intracellular accumulation of the compound, and the high level of selectivity, reflected by a marked uptake into the apoptotic cells, while viable tumor cells remain unstained. TUNEL staining performed on serial sections confirmed that the cells manifesting uptake of NST892 were indeed cells undergoing apoptosis.

Figure 2B:
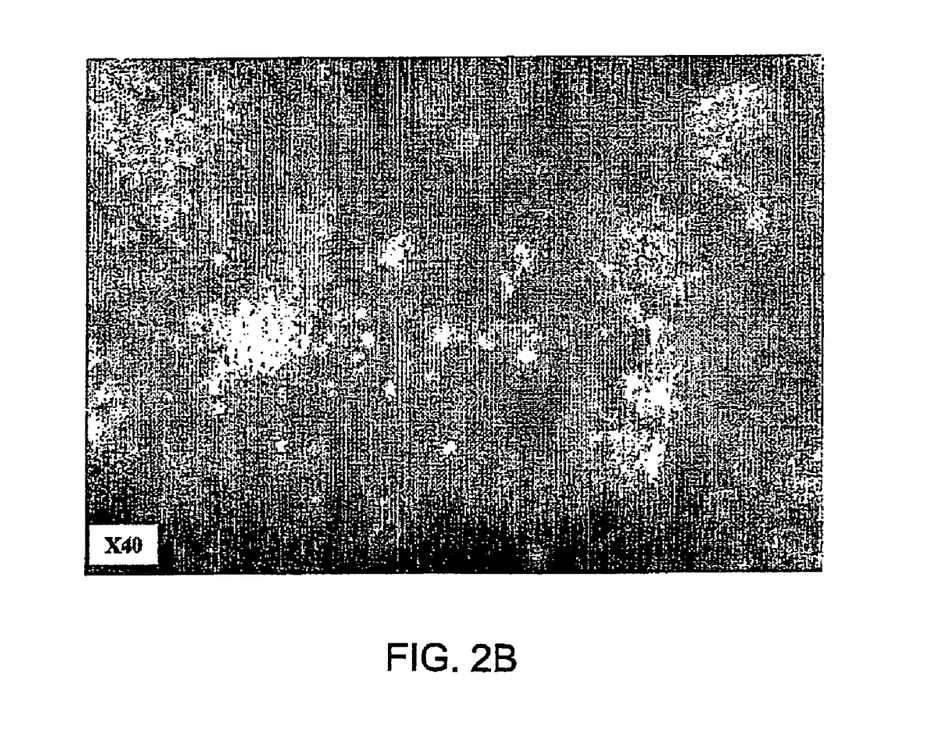

This high level of selectivity is also demonstrated in FIG. 2B, showing fluorescent microscopy of the quiescent surrounding of unstained cells, showing lack of binding of the compound to the normal, viable tissue. Similar results of relatively lack of binding to viable cells were found in various non-target tissues, such as kidney, spleen and muscle.

The invention claimed is:

1. A compound having the structure represented by formula (V):

including pharmaceutically acceptable salts and optical isomers of the structure of formula (V), wherein $R^3$, $R^4$ and $R^6$ may be the same or different, and are each selected from hydrogen; $C_1$, $C_2$, $C_3$, $C_4$, $C_5$ or $C_6$ alkyl; $C_1$, $C_2$, $C_3$, $C_4$, $C_5$ or $C_6$ hydroxyalkyl; and $C_1$, $C_2$, $C_3$, $C_4$, $C_5$ or $C_6$ fluoroalkyl.

2. A compound according to claim 1, wherein $R^3$ and $R^4$ are each a hydrogen and $R^6$ are each a butyl.

3. A compound according to claim 1 having the structure represented by formula (VI):

including pharmaceutically acceptable salts and optical isomers of the structure of formula (VI), wherein b stands for an integer of 2, 3, 4, 5 or 6.

4. A compound according to claim 1 having the structure represented by formula (VII):

(VII)

including pharmaceutically acceptable salts and optical isomers of the structure of formula (VII), wherein m and n each stands independently for an integer of 1, 2, 3 or 4, and k stands for an integer of 2, 3, 4 or 5.

5. A conjugate comprising a compound according to claim 1, being linked either directly or through a linker to a marker for imaging, a pharmaceutically-useful drug or a solid support, wherein said linker is selected from $C_1$, $C_2$, $C_3$ or $C_4$, $C_5$ or $C_6$ alkylene, 5 or 6 atom aromatic or heteroaromatic ring, a metal chelator and combinations thereof.

6. A conjugate according to claim 5, wherein the marker for imaging is for detection by fluorescence, X-ray, computerized tomography (CT scan), magnetic resonance imaging (MRI), radio-isotope scan, single photon emission tomography (SPECT) or positron emission tomography (PET scan).

7. A conjugate according to claim 5, wherein the marker for imaging is Gd, or a radioisotope of a metal selected from Tc, In, Cu, Ga, Xe, Tl and Re, or a radioisotope selected from $^{18}F$, $^{15}O$, $^{18}O$, $^{11}C$, $^{13}C$, $^{124}I$, $^{13}N$ and $^{75}Br$ for PET, and $^{123}I$, $^{131}I$ for SPECT.

8. A conjugate according to claim 5, wherein the marker for imaging is $^{99m}Tc=O$ for SPECT.

9. A method for the detection of PSE-cells within a cell population comprising:
(i) contacting a cell population with a compound according to claim 1; and
(ii) determining the amount of said compound bound to cells, wherein a significant amount of said compound bound to a cell within said cell population indicates its being a PSE cell.

10. A method for the detection of PSE-cells in a patient or an animal, the method comprising:
(i) administering a compound according to claim 1 to the patient or animal; and
(ii) imaging the patient or animal, so as determine the amount of said compound bound to cells, wherein a significant amount of said compound bound to a cell within a cell population indicates its being a PSE-cell.

11. A method for selective targeting of a compound to a PSE cell within a cell population, comprising the step of contacting the cell population comprising said PSE-cell with a compound according to claim 1, thereby selectively targeting the compound to said PSE-cell within said cell population.

12. A method of targeting anticancer drugs to foci of apoptotic cells in a tumor, the method comprising the step of administering a conjugate according to claim 5, comprising a cytotoxic drug, thereby achieving targeting of said drug to the foci of apoptotic cells in said tumor.

13. A method for the detection of PSE-cells within a cell population comprising:
(i) contacting a cell population with a conjugate according to claim 5; and
(ii) determining the amount of said conjugate bound to cells, wherein a significant amount of said conjugate bound to a cell within said cell population indicates its being a PSE cell.

14. A method for the detection of PSE-cells in a patient or an animal, the method comprising:
(i) administering a conjugate according to claim 5 to the patient or animal; and
(ii) imaging the patient or animal, so as to determine the amount of said conjugate bound to cells, wherein a significant amount of said conjugate bound to a cell within said cell population indicates its being a PSE-cell.

15. A method for selective targeting of a conjugate to a PSE cell within a cell population, comprising the step of contacting the cell population comprising said PSE-cell with a conjugate according to claim 5, thereby selectively targeting the conjugate to said PSE-cell within said cell population.

* * * * *

UNITED STATES PATENT AND TRADEMARK OFFICE
CERTIFICATE OF CORRECTION

PATENT NO.       : 7,605,182 B2                                        Page 1 of 1
APPLICATION NO.  : 10/554926
DATED            : October 20, 2009
INVENTOR(S)      : Shirvan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 721 days.

Signed and Sealed this

Fifth Day of October, 2010

David J. Kappos
*Director of the United States Patent and Trademark Office*